United States Patent [19]

Barner et al.

[11] 4,407,754

[45] Oct. 4, 1983

[54] CHOLECALCIFEROL DERIVATIVES

[75] Inventors: Richard Barner, Witterswil; Josef Hubscher, Seon, both of Switzerland

[73] Assignee: Hoffmann-La Roche Inc., Nutley, N.J.

[21] Appl. No.: 357,438

[22] Filed: Mar. 12, 1982

Related U.S. Application Data

[63] Continuation-in-part of Ser. No. 333,354, Dec. 22, 1981, abandoned, which is a continuation of Ser. No. 183,140, Sep. 2, 1980, abandoned.

[30] Foreign Application Priority Data

Sep. 14, 1979 [CH] Switzerland ..................... 8346/79

[51] Int. Cl.$^3$ .............................................. C07J 9/00
[52] U.S. Cl. ......................... 260/239.55 D; 260/397.2

[58] Field of Search .................... 260/397.2, 239.55 D

[56] References Cited

U.S. PATENT DOCUMENTS 4,204,995  5/1980  Barner et al. .................... 260/397.2
4,265,822  5/1981  De Luca et al. ................. 260/397.2
4,268,453  5/1981  Barner et al. .................... 260/397.2

*Primary Examiner*—Elbert L. Roberts
*Attorney, Agent, or Firm*—Jon S. Saxe; Bernard S. Leon; William G. Isgro

[57] ABSTRACT

The vitamin $D_3$ derivative $1\alpha,25,26$-trihydroxycholecalciferol which is useful for regulating the calcium metabolism or calcium transport in the body, cholestene intermediates and a process for their preparation are described.

16 Claims, No Drawings

CHOLECALCIFEROL DERIVATIVES

RELATED APPLICATIONS

This is a continuation-in-part application of copending U.S. patent application Ser. No. 333,354, filed Dec. 22, 1981, now abandoned, which in turn is a continuation of U.S. patent application Ser. No. 183,140, filed Sept. 2, 1980, now abandoned.

BACKGROUND OF THE INVENTION

The present invention relates to a vitamin $D_3$ derivative, namely $1\alpha,25,26$-trihydroxycholecalciferol of the formula

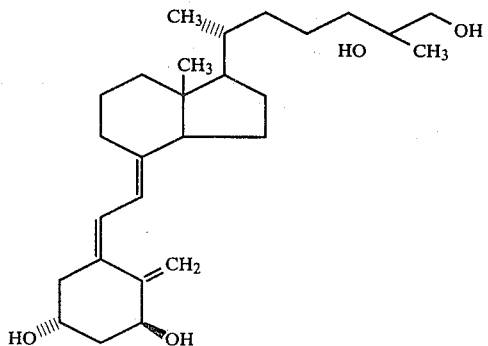

I

The invention also relates to pharmaceutical preparations comprising the compound of formula I, a process for the preparation of the compound of formula I, intermediates, and a process for the preparation of said intermediates.

The compound of formula I is prepared in accordance with the invention by thermally isomerizing the compound of the formula

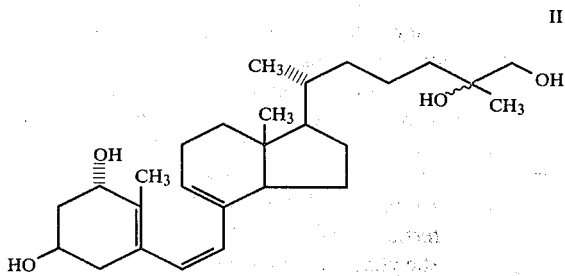

II

This isomerization can be carried out according to the method described in Steroids 24 (1974) 463 for the isomerization of 25,26-dihydroxyprecholecalciferol to 25,26-dihydroxycholecalciferol (e.g., in ethanol at reflux temperature).

The compound of formula II can be prepared by irradiating the compound of the formula

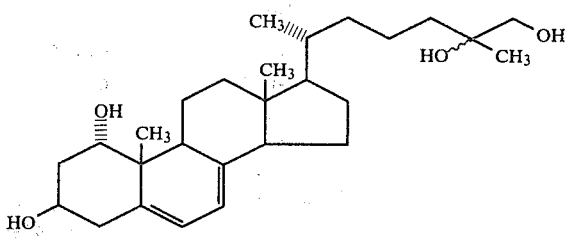

III according to the method described in Steroids 24 (1974) 463 for the irradiation of $3\beta,25,26$-trihydroxycholesta-5,7-diene to 25,26-dihydroxyprecholecalciferol.

The compound of formula III can be prepared by dekatalizing a compound of the formula

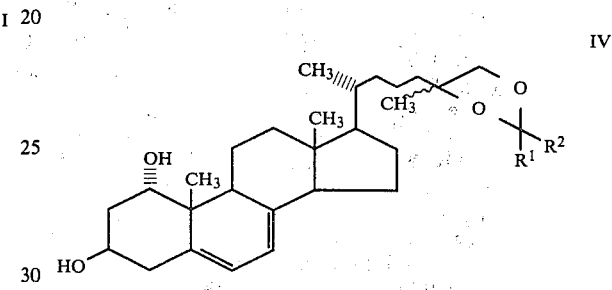

IV wherein $R^1$ and $R^2$ are lower-alkyl; or $R^1$ and $R^2$ taken together are lower-alkylene, according to the method described in German Offenlegungsschrift No. 27 10 062 for the deketalization of 24,25-ketals.

DETAILED DESCRIPTION OF THE INVENTION

As used herein, the term "lower alkyl", alone or in combination, denotes a straight- or branched-chain saturated hydrocarbon group preferably containing from 1 to 6 carbon atoms, for example, methyl, ethyl, propyl, isopropyl, butyl, tert.butyl, pentyl and hexyl. The term "lower alkylene" denotes a straight- or branched-chain organic radical derived from an unsaturated aliphatic hydrocarbon group preferably containing from 1 to 6 carbon atoms, for example, ethylene, propylene, butylene and the like. The term "lower alkoxy" denotes a straight- or branched-chain lower alkyl group attached to the remainder of the molecule by oxygen, for example, methoxy, ethoxy, propoxy, isopropoxy and the like. The term "acetoxy" denotes the residue from the removal of the hydrogen atom of the hydroxy portion of acetic acid. The term "aryl" denotes phenyl or phenyl bearing one or more substituents selected from the group consisting of lower alkyl and lower alkoxy.

In the formulas represented herein, the various substituents are illustrated as joined to the steroid nucleus by one of the following notations: a solid line (———) indicates that a substituent is in the $\beta$-orientation (i.e., above the plane of the molecule) and a broken line (------) indicates that a substituent is in the $\alpha$-orientation (i.e., below the plane of the molecule). A wavy line (∼∼∼∼) indicates the $\alpha$- or $\beta$-orientation.

The compounds of formula IV can be prepared by reacting a compound of the formula

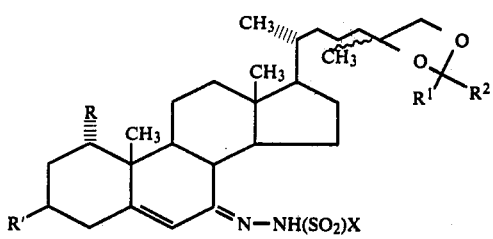

V wherein $R^1$ and $R^2$ are as above; R and R' are etherified or esterified hydroxy readily cleavable to hydroxy; and X is phenyl optionally substituted by lower-alkyl or nitro, with an alkali metal hydride such as lithium hydride in a solvent, preferably a hydrocarbon such as toluene, at a temperature up to reflux temperature.

Ether groups which can be cleaved readily, that is, without affecting other positions of the molecule, are, for example, groups of the formula $R^XO$—$C(R^Y,R^Z)$—O— in which $R^Y$ is hydrogen or lower-alkyl; $R^X$ and $R^Z$ are lower-alkyl; or $R^X$ and $R^Z$ taken together are $C_{3-6}$-alkylene. Examples of such groups are tetrahydropyran-2-yloxy and methoxymethoxy. Examples of esterified hydroxy groups denoted by R and R' are formyloxy and $C_{2-4}$-alkanoyloxy groups such as acetoxy. Examples of groups denoted by X are phenyl, p-nitrophenyl and p-tolyl, preferably the latter.

The compounds of formula V can be prepared by reacting a compound of the formula

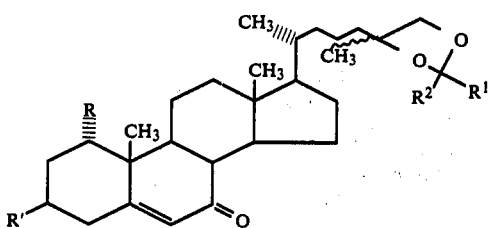

VI with a compound of the formula

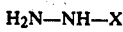

$H_2N$—NH—X    VII wherein X, R, R', $R^1$ and $R^2$ are as above, in a solvent such as methanol at a temperature up to reflux temperature.

The compound of formula VI can be prepared by oxidizing a compound of the formula

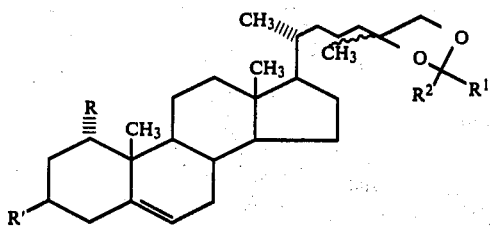

VIII wherein R, R', $R^1$ and $R^2$ are as above, for example, using chromium trioxide in the presence of 3,5-dimethylpyrazole or pyridine in a solvent such as methylene chloride.

The compounds of formula VIII can be prepared by hydrogenating a compound of the formula

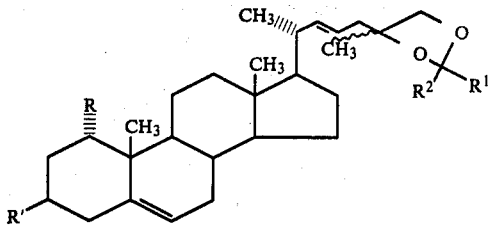

IX wherein R, R', $R^1$ and $R^2$ are as above, for example, using Raney nickel under a hydrogen atmosphere in a solvent such as ethanol.

The compounds of formulas II to VI, VIII and IX also form part of the present invention.

The present invention is also directed to a process for the preparation of the compounds of formula IX.

This process comprises reacting a compound of the formula

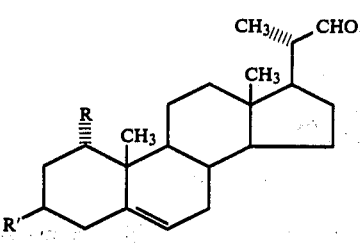

X wherein R and R' are as above, in a Wittig reaction with a compound of the formula

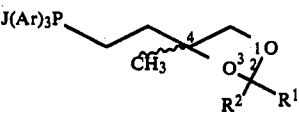

XI wherein Ar is aryl; and $R^1$ and $R^2$ are as above.

The reaction can be carried out under conditions which are known for Wittig reactions. Examples of solvents which can be used are ethers such as tetrahydrofuran, dioxane or diethyl ether or hydrocarbons such as toluene, and examples of bases which can be used are butyl lithium, sodium hydride, sodium amide or potassium tert.butylate.

Preferably, the ylide is manufactured at a low temperature, for example, at −30° C. to −80° C., especially −60° C., in order to exclude the possibility of cleaving the i-steroid grouping.

The reaction of the ylide with a compound of formula X is preferably also carried out at a low temperature, for example, at −20° C. to 0° C., in order to guarantee the preservation of the stereochemistry at C-20.

The compounds of formula XI can be prepared by reacting a compound of the formula

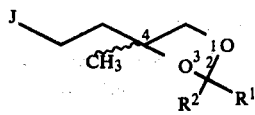

XII wherein R¹ and R² are as above, with a triarylphosphine in an inert organic solvent while warming.

Since the compounds of formula XI begin to be unstable at temperatures above 100° C., the reaction is conveniently carried out at a temperature up to 100° C. in a solvent in which a sufficient reaction velocity is achieved at such a temperature. The preferred solvent is acetonitrile.

The compounds of formula XII can be prepared by reacting a compound of the formula

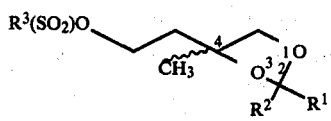

XIII wherein R³ is lower-alkyl or phenyl optionally substituted by lower-alkyl or nitro; and R¹ and R² are as above, with an alkali metal iodide.

The reaction is conveniently carried out in a solvent such as acetone at a temperature of from room temperature up to reflux temperature, preferably at the latter.

The compounds of formula XIII can be prepared by reacting a compound of the formula

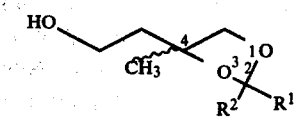

XIV wherein R¹ and R² are as above, with a compound of the formula

  XV wherein R³ is as above; and Z is chlorine, bromine or iodine.

The reaction is conveniently carried out in a solvent such as methylene chloride in the presence of a weak base such as pyridine at a temperature of 0° C.

The C-atom in position 25 in the compounds of formulas I to VI, VIII and IX and the C-atom in the position 4 in the compounds of formulas XII to XIV have the R- or the S-configuration. In addition, the 22,23-double bond in a compound of formula IX can have the E- or the Z-configuration. The aforementioned compounds can, however, also exist in the form of mixtures of the R- and S-forms or of mixtures of the E- and Z-forms. R¹ and R² preferably are methyl in the compounds of formulas IV to VI, VIII, IX and XI to XIV, and R and R' preferably are acetoxy in the compounds of formulas V, VI, VIII and IX.

The compound of formula I has similar properties to other biologically-active metabolites of vitamin D₃, for example, 25,26-dihydroxycholecalciferol, and can therefore, in principle, be administered in the same manner and dosage as the said metabolites, for example, for regulating the calcium metabolism or calcium transport in the body. The compounds of formula I is useful especially for the treatment of patients with kidney failure or kidney insufficiency. The R- and S-epimers of the compound of formula I lower the serum level of 1α,25-dihydroxycholecalciferol. Additionally, both the R- and S-epimers promote bone mineralization in vitamin D-deficient animals, but only the R-epimer promotes bone mineralization in disodium-ethane-1-hydroxy-1,1-diphosphinate-blocked animals. The R- and S-epimers are useful for treatment of disease states which are characterized by higher-than-normal serum levels of the endogenously-produced active vitamin D₃ metabolite 1α,25-dihydroxycholecalciferol or in conditions in which there is an increased sensitivity to 1α,25-dihydroxycholecalciferol. Specifically included among the disease states for which the compound of formula I is indicated are hypercalcemia, sarcoidosis, hypercalciuria, nephrolithiasis and nephrocalcinosis.

The compound of formula I can be used as a medicament; for example, in the form of pharmaceutical preparations which contain it in association with a pharmaceutical, organic or inorganic inert carrier material which is suitable for enteral or parenteral administration such as water, gelatin, gum arabic, lactose, starch, magnesium stearate, talc, vegetable oils, polyalkyleneglycols and the like. The pharmaceutical preparations can be made up in solid form, for example, as tablets, dragees, suppositories or capsules, or in a liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. They can also contain still other therapeutically-valuable substances.

The following examples further illustrate the invention:

EXAMPLE 1

1α,25(R,S),26-Trihydroxy-22-Dehydrocholesterol-25,26-Acetonide-1,3-Diacetate 2.303 g of (R,S)-[2-(2,2,4-trimethyl-1,3-dioxolan-4-yl)-ethyl]-triphenylphosphonium iodide were mixed with 10 ml of tetrahydrofuran under argon. 2.5 ml of butyl lithium as a 2 molar solution in hexane were added dropwise at −78° C., and the mixture was stirred for 1.5 hours. To the resulting solution there were added dropwise at −60° C. 1.10 g of a solution of (20S)-1α,3β-diacetoxy-20-formyl-pregn-5-ene in tetrahydrofuran. After 30 minutes, the mixture was left to stand at room temperature and stirred overnight. Then, water was added, and the mixture was extracted with ether. After drying, concentration and chromatography on 100 g of silica gel with hexane/ether/ethyl acetate (4:4:1), there were obtained 0.69 g (47%) of 1α,25(R,S),26-trihydroxy-22-dehydrocholesterol-25,26-acetonide-1,3-diacetate.

The aforementioned phosphonium iodide can be prepared as follows:

4.38 g of 2-methylbutane-1,2,4-triol-1,2-acetonide and 5.50 g of tosyl chloride were dissolved in 10 ml of methylene chloride. 4 ml of pyridine were added dropwise at 0° C., and the mixture was then left to stand at 0° C. for 1 hour and at room temperature for 1 hour. After the addition of 100 g of ice and then of 100 ml of 1 N sulfuric acid, the mixture was extracted with methylene chloride. After drying and concentration, there were obtained 6.5 g (97%) of 4-(2-tosyloxyethyl)-2,2,4-trimethyl-1,3-dioxolane.

6.5 g of 4-(2-tosyloxyethyl)-2,2,4-trimethyl-1,3-dioxolane were heated at reflux temperature for 1 hour with 50 g of sodium iodide and 500 ml of acetone, then concentrated, suspended in 100 ml of toluene and filtered. The toluene solution was washed with sodium thiosulphate solution, dried and concentrated. There were obtained 6.0 g (97%) of 4-(2-iodoethyl)-2,2,4-trimethyl-1,3-dioxolane.

6.0 g of 4-(2-iodoethyl)-2,2,4-trimethyl-1,3-dioxolane and 10 g of triphenylphosphine were dissolved in 200 ml of acetonitrile and heated at reflux temperature for 70 hours. The yellow solution was concentrated, mixed with ether, left to stand, then washed with ether and dried in a high vacuum. There were obtained 10.6 g (91%) of (R,S)-[2-(2,2,4-trimethyl-1,3-dioxolan-4-yl)-ethyl]-triphenylphosphonium iodide in the form of hygroscopic crystals of melting point 49° to 50° C.

EXAMPLE 2

1α,25(R,S),26-Trihydroxy-22-Dehydrocholesterol-25,26-Acetonide-1,3-Diacetate 0.94 g of (R,S)-[2-(2,2,4-trimethyl-1,3-dioxolan-4-yl)-ethyl]-triphenylphosphonium iodide were dissolved in 10 ml of tetrahydrofuran under argon. 2.5 ml of butyl lithium (2 molar in hexane) were added dropwise at −30° C. The mixture was stirred for 2 hours. A solution of 0.40 g of (20S)-1α,3β-diacetoxy-20-formyl-pregn-5-ene in 1 ml of tetrahydrofuran at the same temperature as before. The mixture was stirred at room temperature overnight. After working up in a manner analogous to that described in Example 1, there were obtained 321 mg (78%) of 1α,25(R,S),26-trihydroxy-22-dehydrocholesterol-25,26-acetonide-1,3-diacetate.

EXAMPLE 3

1α,25(R,S),26-Trihydroxycholesterol-25,26-Acetonide-1,3-Diacetate 61 mg of 1α,25(R,S),26-trihydroxy-22-dehydrocholesterol-25,26-acetonide-1,3-diacetate were dissolved in 10 ml of ethanol and shaked for 8 hours with Raney nickel under a hydrogen atmosphere. After filtration and concentration, there were obtained 64 mg (100%) of 1α,25(R,S),26-trihydroxycholesterol-25,26-acetonide-1,3-diacetate; $[\alpha]_D^{20} = -13.6°$ (c=0.55% in chloroform).

EXAMPLE 4

7-Keto-1α,25(R,S),26-Trihydroxycholesterol-25,26-Acetonide-1,3-Diacetate 1.4 g of chromium trioxide were suspended in 10 ml of methylene chloride. 1.4 g of 3,5-dimethylpyrazole were added thereto at −20° C. The mixture was then stirred for 15 minutes. Then, a solution of 0.55 g of 1α,25(R,S),26-trihydroxycholesterol-25,26-acetonide-1,3-diacetate in 1 ml of methylene chloride was added dropwise. The mixture was stirred at −20° C. for 1 hour and at room temperature for 3 hours, then the solution was treated with 20 ml of ether, filtered, washed with ether, concentrated and purified on silica gel with toluene/ethyl acetate (2:1). There were obtained 0.35 g (62%) of 7-keto-1α,25(R,S),26-trihydroxycholesterol-25,26-acetonide-1,3-diacetate.

EXAMPLE 5

1α,25(R,S),26-Trihydroxycholesterol-25,26-Acetonide-1,3-Diacetate-7-Tosylhydrazone 0.35 g of 7-keto-1α,25(R,S),26-trihydroxycholesterol-25,26-acetonide-1,3-diacetate and 0.32 g of tosyl hydrazine were dissolved in 10 ml of methanol. The mixture was heated at reflux temperature for 5 hours, then concentrated and chromatographed on silica gel with toluene/ethyl acetate (2:1). There were obtained 0.45 g (100%) of 1α,25(R,S),26-trihydroxycholesterol-25,26-acetonide-1,3-diacetate-7-tosylhydrazone.

EXAMPLE 6

1α,25(R,S),26-Trihydroxy-7-Dehydrocholesterol-25,26-Acetonide 0.45 g of 1α,25(R,S),26-trihydroxycholesterol-25,26-acetonide-1,3-diacetate-7-tosylhydrazone were dissolved in 20 ml of toluene and heated at reflux temperature for 2 hours with 0.50 g of lithium hydride. 10 ml of methanol and 10 g of ice were added at 0° C. The mixture was extracted with ethyl acetate, the organic phase was dried with magnesium sulfate and, after concentration, chromatographed on silica gel with toluene/ethyl acetate 2:1. There were obtained 0.20 g (70%) of 1α,25(R,S),26-trihydroxy-7-dehydrocholesterol-25,26-acetonide.

EXAMPLE 7

1α,25(R,S),26-Trihydroxy-7-Dehydrocholesterol 0.20 g of 1α,25(R,S),26,trihydroxy-7-dehydrocholesterol-25,26-acetonide were dissolved in 30 ml of methanol and stirred at room temperature for 3 hours with 2 g of acid ion-exchanger. Then, the mixture was filtered and concentrated to give 0.15 g (82%) of crude product. Crystallization from methylene chloride gave 80 mg (44%) of 1α,25(R,S),26-trihydroxy-7-dehydrocholesterol of melting point 124° to 126° C.

The provitamin obtained was converted according to the method described in Steroids 24 (1974) 463 via 1α,25(R,S),26-trihydroxyprecholecalciferol into 1α,25(R,S),26-trihydroxycholecalciferol; UV in 95% ethanol, $\lambda_{max}$ 266 nm, $\lambda_{min}$ 228 nm; TLC [ethyl acetate/methanol (9:1)], Rf=0.32.

What is claimed is:

1. 1α,25,26-trihydroxyprecholecalciferol as characterized by the formula

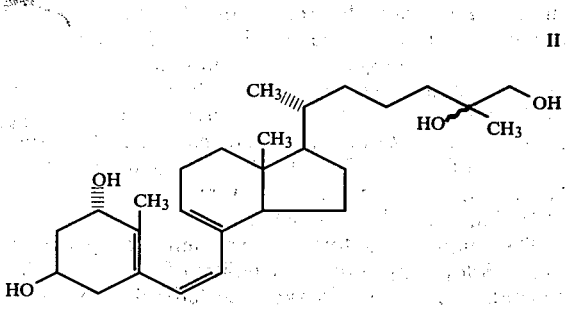

II

2. The compound in accordance with claim 1 which is 1α,25(R,S),26-trihydroxyprecholecalciferol.

3. 1α,25,26-trihydroxy-7-dehydrocholesterol as characterized by the formula

III

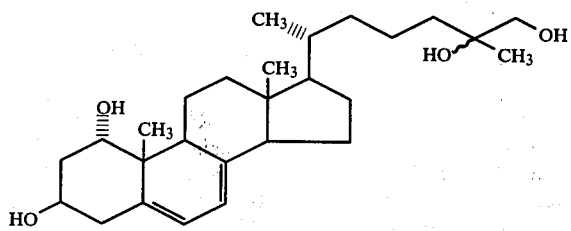

4. The compound in accordance with claim 3 which is 1α,25(R,S),26-trihydroxy-7-dehydrocholesterol.

5. A cholestadiene of the formula

IV

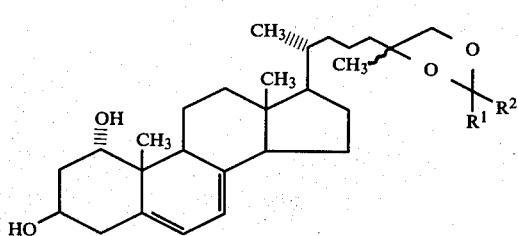

wherein $R^1$ and $R^2$ are lower-alkyl or $R^1$ and $R^2$ together are lower-alkylene.

6. The compound in accordance with claim 5 which is 1α,25(R,S),26-trihydroxy-7-dehydrocholesterol-25,26-acetonide.

7. A cholestene of the formula

V

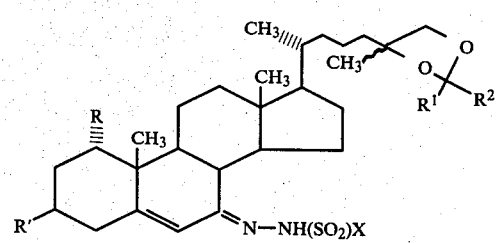

wherein $R^1$ and $R^2$ are lower-alkyl or $R^1$ and $R^2$ together are lower-alkylene; R and R' are etherified or esterified hydroxy readily cleavable to hydroxy; and X is phenyl optionally substituted by lower-alkyl or nitro.

8. The compound in accordance with claim 7 which is 1α,25(R,S),26-trihydroxycholesterol-25,26-acetonide-1,3-diacetate-7-tosylhydrazone.

9. A cholestene of the formula

VI

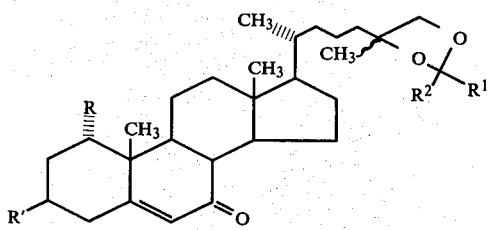

wherein $R^1$ and $R^2$ are lower-alkyl or $R^1$ and $R^2$ together are lower-alkylene; and R and R' are etherified or esterified hydroxy readily cleavable to hydroxy.

10. The compound in accordance with claim 9 which is 7-keto-1α,25(R,S),26-trihydroxycholesterol-25,26-acetonide-1,3-diacetate.

11. A cholestene of the formula

VIII

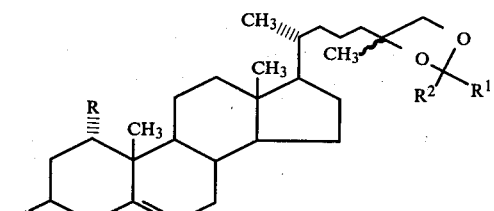

wherein $R^1$ and $R^2$ are lower-alkyl or $R^1$ and $R^2$ together are lower-alkylene; and R and R' are etherified or esterified hydroxy readily cleavable to hydroxy.

12. The compound in accordance with claim 11 which is 1α,25(R,S),26-trihydroxycholesterol-25,26-acetonide-1,3-diacetate.

13. A cholestene of the formula

IX

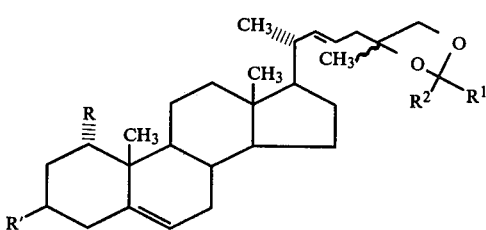

wherein $R^1$ and $R^2$ are lower-alkyl or $R^1$ and $R^2$ together are lower-alkylene; and R and R' are etherified or esterified hydroxy readily cleavable to hydroxy.

14. The compound in accordance with claim 13 which is 1α,25(R,S),26-trihydroxy-22-dehydrocholesterol-25,26-acetonide-1,3-diacetate.

15. A process for the manufacture of the cholestadienes of the formula

IX

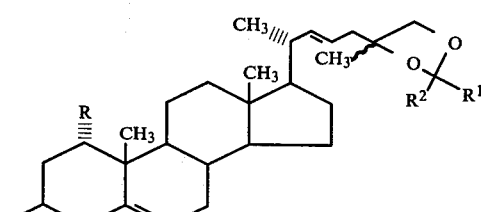

wherein $R^1$ and $R^2$ are lower-alkyl or $R^1$ and $R^2$ together are lower-alkylene; and R and R' are etherified or esterified hydroxy readily cleavable to hydroxy, which process comprises reacting a compound of the formula

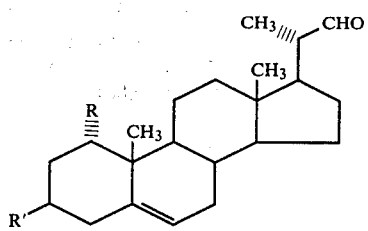

wherein R and R' have the significance given earlier in this claim, in a Wittig reaction with a compound of the formula

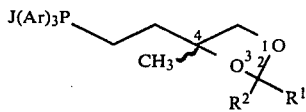

wherein Ar is an aryl group; and $R^1$ and $R^2$ have the significance given earlier in this claim.

16. A process according to claim 15 wherein (R,S)-[(2,2,4-trimethyl-1,3-dioxolan-4-yl)ethyl]triphenylphosphonium iodide is converted at a temperature between $-30°$ C. and $-80°$ C. with butyl lithium into the ylid, and this is reacted with (20S)-1α,3β-diacetoxy-20-formyl-pregn-5-ene.

* * * * *